(12) United States Patent
Crawford et al.

(10) Patent No.: US 9,339,575 B2
(45) Date of Patent: *May 17, 2016

(54) STERILIZATION PROCESS DESIGN FOR A MEDICAL ADHESIVE

(71) Applicant: Covidien LP, Mansfield, MA (US)

(72) Inventors: Don Crawford, Louisville, TN (US); Rodney Raabe, Spokane, WA (US); Jack Chu, Santa Rosa, CA (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/796,098

(22) Filed: Jul. 10, 2015

(65) Prior Publication Data

US 2015/0314022 A1 Nov. 5, 2015

Related U.S. Application Data

(63) Continuation of application No. 14/323,962, filed on Jul. 3, 2014, now Pat. No. 9,084,835, which is a continuation of application No. 13/775,014, filed on Feb. 22, 2013, now Pat. No. 8,808,620.

(60) Provisional application No. 61/601,718, filed on Feb. 22, 2012.

(51) Int. Cl.
| | |
|---|---|
| A61L 2/08 | (2006.01) |
| A61L 2/28 | (2006.01) |
| A61L 2/04 | (2006.01) |
| A61L 2/07 | (2006.01) |
| A61L 2/20 | (2006.01) |

(52) U.S. Cl.
CPC ... *A61L 2/28* (2013.01); *A61L 2/04* (2013.01); *A61L 2/07* (2013.01); *A61L 2/206* (2013.01); *A61L 2202/24* (2013.01)

(58) Field of Classification Search
CPC .................................. A61L 2/08; A61L 2/04
USPC ........................................................ 422/22
See application file for complete search history.

(56) References Cited

U.S. PATENT DOCUMENTS

| | | | |
|---|---|---|---|
| 3,699,127 | A | 10/1972 | O'Sullivan et al. |
| 3,834,394 | A | 9/1974 | Hunter et al. |

(Continued)

FOREIGN PATENT DOCUMENTS

| | | |
|---|---|---|
| CN | 2735942 Y | 10/2005 |
| CN | 201101549 Y | 8/2008 |

(Continued)

OTHER PUBLICATIONS

"Bacillus Atrophaeus Spores," Autoclave Testing Service, Inc. www.autoclavesporetesting.com-Bacillus_Atrophaeus_Spores.htm, webpage from Internet Archive Wayback Machine: https:--archive.org-web-., Jul. 6, 2010, 2 pp.

(Continued)

*Primary Examiner* — Sean E Conley

(57) ABSTRACT

Medical devices, including medical adhesives, need to be sterile before application to a patient. A dry heat sterilization process can sterilize medical adhesives for patient application. The dry heat sterilization process can be validated for particular equipment arrangements and medical adhesives being utilized.

20 Claims, 9 Drawing Sheets

(56) References Cited

U.S. PATENT DOCUMENTS

| | | |
|---|---|---|
| 4,038,345 A | 7/1977 | O'Sullivan et al. |
| 4,039,665 A | 8/1977 | Foley |
| 4,085,757 A | 4/1978 | Pevsner |
| 4,102,945 A | 7/1978 | Gleave |
| 4,125,494 A | 11/1978 | Schoenberg et al. |
| 4,213,461 A | 7/1980 | Pevsner |
| 4,268,495 A | 5/1981 | Muxfeldt et al. |
| 4,582,061 A | 4/1986 | Fry |
| RE32,348 E | 2/1987 | Pevsner |
| 4,705,517 A | 11/1987 | DiPisa, Jr. |
| 4,805,628 A | 2/1989 | Fry et al. |
| 4,994,069 A | 2/1991 | Ritchart et al. |
| 4,997,861 A | 3/1991 | Hechenberger et al. |
| 5,022,399 A | 6/1991 | Biegeleisen |
| 5,034,456 A | 7/1991 | Katsumura et al. |
| 5,327,891 A | 7/1994 | Rammler |
| 5,382,261 A | 1/1995 | Palmaz |
| 5,383,466 A | 1/1995 | Partika |
| 5,456,693 A | 10/1995 | Conston et al. |
| 5,480,935 A | 1/1996 | Greff et al. |
| 5,520,653 A | 5/1996 | Reilly et al. |
| 5,536,490 A | 7/1996 | Klaveness et al. |
| 5,656,036 A | 8/1997 | Palmaz |
| 5,665,817 A | 9/1997 | Greff et al. |
| 5,667,767 A | 9/1997 | Greff et al. |
| 5,676,962 A | 10/1997 | Garrido et al. |
| 5,733,294 A | 3/1998 | Forber et al. |
| 5,814,016 A | 9/1998 | Valley et al. |
| 5,830,222 A | 11/1998 | Makower |
| 5,851,508 A | 12/1998 | Greff et al. |
| 5,868,703 A | 2/1999 | Bertolero et al. |
| 5,874,044 A | 2/1999 | Kotzev |
| 5,981,621 A | 11/1999 | Clark et al. |
| 6,013,053 A | 1/2000 | Bower et al. |
| 6,106,806 A | 8/2000 | Klaveness et al. |
| 6,136,326 A | 10/2000 | Kotzev |
| 6,143,352 A | 11/2000 | Clark et al. |
| 6,143,805 A | 11/2000 | Hickey et al. |
| 6,190,353 B1 | 2/2001 | Makower et al. |
| 6,191,202 B1 | 2/2001 | Greff et al. |
| 6,260,737 B1 | 7/2001 | Gruendeman et al. |
| 6,322,548 B1 | 11/2001 | Payne et al. |
| 6,323,275 B2 | 11/2001 | Takahashi et al. |
| 6,412,639 B1 * | 7/2002 | Hickey ............... 206/570 |
| 6,433,096 B1 | 8/2002 | Hickey et al. |
| 6,443,941 B1 | 9/2002 | Slepian et al. |
| 6,565,840 B1 | 5/2003 | Clark et al. |
| 6,572,873 B1 | 6/2003 | Osman et al. |
| 6,579,311 B1 | 6/2003 | Makower |
| 6,579,916 B1 | 6/2003 | Askill et al. |
| 6,607,512 B2 | 8/2003 | Oliver et al. |
| 6,616,675 B1 | 9/2003 | Evard et al. |
| 6,638,293 B1 | 10/2003 | Makower et al. |
| 6,655,386 B1 | 12/2003 | Makower et al. |
| 6,695,787 B2 | 2/2004 | Hogendijk et al. |
| 6,699,928 B2 | 3/2004 | Cobbley et al. |
| 6,723,052 B2 | 4/2004 | Mills |
| 6,726,674 B2 | 4/2004 | Leu |
| 6,743,858 B2 | 6/2004 | Hickey et al. |
| 7,077,836 B2 | 7/2006 | Lary et al. |
| 7,083,634 B2 | 8/2006 | Shalaby |
| 7,094,216 B2 | 8/2006 | Trombley, III et al. |
| 7,134,438 B2 | 11/2006 | Makower et al. |
| 7,201,758 B2 | 4/2007 | Farmache |
| 7,229,413 B2 | 6/2007 | Violante et al. |
| 7,235,052 B2 | 6/2007 | Kellar et al. |
| 7,258,669 B2 | 8/2007 | Russell |
| 7,314,466 B2 | 1/2008 | Lary et al. |
| 7,351,426 B2 | 4/2008 | Shalaby et al. |
| 7,371,345 B2 | 5/2008 | Stewart et al. |
| 7,402,320 B2 | 7/2008 | Mirizzi et al. |
| 7,648,527 B2 | 1/2010 | Agnew et al. |
| 7,687,053 B2 | 3/2010 | Porter |
| 7,772,306 B2 | 8/2010 | Blacklock et al. |
| 7,932,305 B2 | 4/2011 | Badejo et al. |
| 8,029,560 B2 | 10/2011 | Bates et al. |
| 8,092,390 B2 | 1/2012 | Field |
| 8,110,144 B2 * | 2/2012 | Morales ............... 422/1 |
| 8,173,722 B2 | 5/2012 | Baiker et al. |
| 8,192,731 B2 | 6/2012 | Misiak et al. |
| 8,198,344 B2 | 6/2012 | Zhang et al. |
| 8,287,687 B1 | 10/2012 | Schueneman et al. |
| 8,293,838 B2 | 10/2012 | Zhang et al. |
| 8,313,533 B2 | 11/2012 | Goldmann |
| 8,398,596 B2 | 3/2013 | Field |
| 8,475,492 B2 | 7/2013 | Raabe et al. |
| 8,491,881 B2 | 7/2013 | Salamone et al. |
| 8,518,104 B2 | 8/2013 | Bates et al. |
| 8,541,495 B2 | 9/2013 | Ishizaki et al. |
| 8,808,620 B1 * | 8/2014 | Chu et al. ............... 422/22 |
| 8,845,614 B2 | 9/2014 | Raabe et al. |
| 9,084,835 B2 | 7/2015 | Crawford et al. |
| 2002/0177772 A1 | 11/2002 | Altman et al. |
| 2002/0188195 A1 | 12/2002 | Mills |
| 2003/0012735 A1 | 1/2003 | Unger et al. |
| 2003/0050531 A1 | 3/2003 | Field |
| 2003/0065266 A1 | 4/2003 | Russell |
| 2003/0186005 A1 | 10/2003 | Rivera et al. |
| 2003/0202956 A1 | 10/2003 | Clark et al. |
| 2003/0206864 A1 | 11/2003 | Mangin |
| 2004/0068190 A1 | 4/2004 | Cespedes |
| 2004/0073238 A1 | 4/2004 | Makower |
| 2004/0098030 A1 | 5/2004 | Makower et al. |
| 2004/0193055 A1 | 9/2004 | Field et al. |
| 2004/0230119 A1 | 11/2004 | Brustad et al. |
| 2005/0113798 A1 | 5/2005 | Slater et al. |
| 2005/0137575 A1 | 6/2005 | Thompson et al. |
| 2005/0273074 A1 | 12/2005 | Lewis |
| 2006/0030808 A1 | 2/2006 | Kennedy |
| 2006/0052822 A1 | 3/2006 | Mirizzi et al. |
| 2006/0052823 A1 | 3/2006 | Mirizzi et al. |
| 2006/0062687 A1 | 3/2006 | Morales |
| 2006/0195134 A1 | 8/2006 | Crittenden |
| 2006/0276743 A1 | 12/2006 | MacMahon et al. |
| 2007/0021730 A1 | 1/2007 | Flaherty et al. |
| 2007/0078207 A1 * | 4/2007 | Jonn et al. ............... 524/347 |
| 2007/0208417 A1 | 9/2007 | Agnew |
| 2007/0248486 A1 | 10/2007 | Morales |
| 2007/0255140 A1 | 11/2007 | Violante et al. |
| 2007/0265370 A1 | 11/2007 | Anitua Aldecoa |
| 2007/0292472 A1 | 12/2007 | Paul et al. |
| 2008/0021139 A1 | 1/2008 | Blacklock et al. |
| 2008/0039548 A1 | 2/2008 | Zavatsky et al. |
| 2008/0045996 A1 | 2/2008 | Makower et al. |
| 2008/0103456 A1 | 5/2008 | Johnson et al. |
| 2008/0154136 A1 | 6/2008 | Webler |
| 2008/0241249 A1 | 10/2008 | Quintero et al. |
| 2008/0269720 A1 | 10/2008 | Sabbah |
| 2008/0311323 A1 | 12/2008 | Morales |
| 2009/0131938 A1 | 5/2009 | Khatri et al. |
| 2009/0257976 A1 | 10/2009 | Kerber et al. |
| 2009/0264769 A1 | 10/2009 | Sadaka |
| 2010/0144895 A1 | 6/2010 | Porter |
| 2010/0213096 A1 | 8/2010 | Morales |
| 2010/0217306 A1 | 8/2010 | Raabe et al. |
| 2010/0217313 A1 | 8/2010 | Raabe et al. |
| 2010/0239505 A1 | 9/2010 | Reichl et al. |
| 2011/0060277 A1 | 3/2011 | Lilley |
| 2011/0098564 A1 | 4/2011 | Larson et al. |
| 2011/0172488 A1 | 7/2011 | Field |
| 2011/0178399 A1 | 7/2011 | Del Corso |
| 2011/0224538 A1 | 9/2011 | Linares |
| 2011/0224723 A1 | 9/2011 | Lee et al. |
| 2011/0251318 A1 | 10/2011 | Ishizaki et al. |
| 2011/0269870 A1 | 11/2011 | Cohn et al. |
| 2012/0027821 A1 | 2/2012 | Shirotake et al. |
| 2012/0064027 A1 | 3/2012 | Shalaby |
| 2012/0109191 A1 | 5/2012 | Marano et al. |
| 2012/0128903 A1 | 5/2012 | Morales |
| 2013/0011589 A1 | 1/2013 | Morales |
| 2013/0052152 A1 | 2/2013 | Keplinger |
| 2013/0072907 A1 | 3/2013 | Lichty, II et al. |
| 2013/0085384 A1 | 4/2013 | Field |
| 2013/0095262 A2 | 4/2013 | Morales |

(56) References Cited

U.S. PATENT DOCUMENTS

| | | | |
|---|---|---|---|
| 2013/0116633 | A1 | 5/2013 | Lichty et al. |
| 2013/0144159 | A1 | 6/2013 | Field et al. |
| 2013/0150712 | A1 | 6/2013 | Field |
| 2013/0156824 | A1 | 6/2013 | Keplinger |
| 2013/0204232 | A1 | 8/2013 | Wieser et al. |
| 2013/0225640 | A1 | 8/2013 | Kim |
| 2013/0267942 | A1 | 10/2013 | Fulton, III et al. |
| 2013/0281835 | A1 | 10/2013 | Field et al. |
| 2013/0303654 | A1 | 11/2013 | Salamone et al. |
| 2015/0018867 | A1 | 1/2015 | Raabe et al. |
| 2015/0044091 | A1 | 2/2015 | Morales |

FOREIGN PATENT DOCUMENTS

| | | | |
|---|---|---|---|
| EP | 1230313 | A1 | 8/2002 |
| EP | 1206291 | B1 | 10/2005 |
| EP | 2162139 | A1 | 3/2010 |
| EP | 2303342 | A2 | 4/2011 |
| EP | 2303343 | A2 | 4/2011 |
| JP | 2000290600 | A | 10/2000 |
| JP | 2006523471 | A | 10/2006 |
| WO | 8606738 | A1 | 11/1986 |
| WO | 2004071612 | A2 | 8/2004 |
| WO | 2010033406 | A2 | 3/2010 |
| WO | 2013013080 | A1 | 1/2013 |

OTHER PUBLICATIONS

"Biological Indicators and Inoculated Carriers," NAMSA—Medical Device Testing Laboratory and Contract Research Organization, www.namsa.com-products-biological.com, webpage from Internet Archive Wayback Machine https:--archive.org-web-., Jul. 30, 2010, 1 pp.

"Dry Heat Sterilizers," Autoclave Testing Service, Inc., www.autoclavesporetesting.com-Dry_heat_sterilization.com, webpage from Internet Archive Wayback Machine: https:--archive.org-web-., Jul. 4, 2010, 2 pp.

"Monitoring the Effectiveness of the Sterilization Process", Sterile Processing University 2007, www.spdceus.com-monitoring_sterilization_process.com, webpage from Internet Archive Wayback Machine: https:--archive.org-web-., Nov. 28, 2010, 6 pp.

"Process Validation: Moist Heat Sterilization for Pharmaceuticals," Health Canada, retrieved online http:/ /www.hc-sc.gc.ca/dhp-mps/compli-conform/gmp-bpf/validation/mhsp-schpp- eng.php, Mar. 1, 2001, 20 pp.

"Steps of Dry-Heat Sterilization," Engender Health www.engenderhealth.org-ip-instrum-inm11.com, webpage from Internet Archive Wayback Machine: https:--archive.org-web-., Aug. 13, 2010, 1 pp.

"Sterility Assurance for Industry & Healthcare," Raven Labs Products and Services, Mesa Laboratories, Inc., www.mesalabs.com-products-services-raven-labs.com, webpage from Internet Archive Wayback Machine: https:--archive.org-web-., Jul. 30, 2010, 3 pp.

"Sterilization—An Overview", Pacific BioLabs, 2004 PowerPoint Presentation, www.pacificbiolabs.com-tech_downloads.asp, webpage from Internet Archive Wayback Machine: https:-- archive.org-web-., Sep. 26, 2010, 37 pp.

"Validating Heat Sterilization," Pacific BioLabs, 2007 PowerPoint Presentation, www.pacificbiolabs.com-tech_downloads.asp, webpage from Internet Archive Wayback Machine: https:--archive.org-web-., Sep. 26, 2010, 38 pp.

Case et al., "Dry Heat Sterilization and Depyrogenation Validation and Monitoring," Agalloco et al. ed., Validation of Pharmaceutical Processes, 3rd Edition, Informa Healthcare USA, Inc., 2008, pp. 223-240.

Chieppo et al., "Sterilization: Dry Heat," Swarbrick, ed., Encyclopedia of Pharmaceutical Technology, 3rd Ed., vol. 6, Informa Healthcare USA, Inc., Chapter 252, 2007, pp. 3512-3518.

Darmady et al., "Sterilization by Dry Heat," J. Clin. Path. 14, 1961, lecture given on Feb. 2, 1960, pp. 38-44.

Gillis et al., "Understanding Biological Indicator Grow-Out Times," Pharmaceutical Technology, vol. 34, No. 1, Jan. 2010, 8 pp.

Joslyn, "Sterilization by Heat," Block, ed., Disinfection, Sterilization, and Preservation, 5th Ed., Lippincott Williams & Wilkins, Chapter 36, 2001, pp. 695-728.

Merritt, "Sterilization Process for a Medical Adhesive," Senior Project submitted in partial fulfillment for Bachelor of Science in Manufacturing Engineering, California Polytechnic State University, San Luis Obispo, Jul. 11, 2011, pp. 1-45.

Pistolesi, "Sterilization: Moist Heat," Swarbrick, ed., Encyclopedia of Pharmaceutical Technology, 3rd Ed., vol. 6, Informa Healthcare USA, Inc., Chapter 252, 2007, pp. 3529-3539.

Tietjen et al., "Sterilization," Infection Prevention Guidelines for Healthcare Facilities with Limited Resources, Chapter 11, 1992, JHPIEGO Corporation, 2003, www.reproline.jhu.edu-english-4morerh-4ip-IP_manual-11_Sterilization.pdf, 14 pp.

Sasaki et al., "Evaluation of High-Temperature and Short-Time Sterilization of Injection Ampules by Microwave Heating," PDA Journal of Pharmaceutical Science and Technology, vol. 21, No. 1, Jan./Feb. 1998, pp. 5-12 (Abstract Only).

Sasaki et al., "Microwave Continuous Sterilization of Injection Ampoules," PDA Journal of Pharmaceutical Science and Technology, vol. 50, No. 3, May-Jun. 1996, pp. 172-179 (Abstract Only).

Sasaki et al., "Validation of a Microwave Sterilizer for Injection Ampules," PDA Journal of Pharmaceutical Science and Technology, 1999, pp. 60-69.

Solanki et al., "Microwave Technology—A Potential Tool in Pharmaceutical Science," International Journal of PharmTech Research, vol. 2, No. 3, Jul.-Sep. 2010, pp. 1754-1761.

International Search Report and Written Opinion in PCT Application No. PCT/US12/047460, dated Dec. 21, 2012.

U.S. Appl. No. 13/470,200, by Jack Chu, filed May 11, 2012.

U.S. Appl. No. 13/842,722, by Choi, filed Mar. 15, 2013.

Prosecution History from U.S. Pat. No. 8,808,620, dated Dec. 3, 2013 through Jun. 27, 2014, 30 pp.

Prosecution History from U.S. Pat. No. 9,084,835, dated Jul. 3, 2014 through Mar. 16, 2015, 89 pp.

* cited by examiner

STERILIZATION PROCESS DESIGN FOR A MEDICAL ADHESIVE

CROSS-REFERENCE TO RELATED APPLICATIONS

This application is a continuation of U.S. application Ser. No. 14/323,926, filed Jul. 3, 2014, titled STERILIZATION PROCESS DESIGN FOR A MEDICAL ADHESIVE, which is a continuation of U.S. application Ser. No. 13/775,014, filed Feb. 22, 2013, now U.S. Pat. No. 8,808,620, titled STERILIZATION PROCESS DESIGN FOR A MEDICAL ADHESIVE, which claims the benefit under 35 U.S.C. §119 (e) as a nonprovisional of U.S. Provisional Application No. 61/601,718, filed Feb. 22, 2012, titled STERILIZATION PROCESS DESIGN FOR A MEDICAL ADHESIVE, the entirety of each of which is incorporated herein by reference and made a part of this specification.

BACKGROUND

1. Field

This disclosure generally relates to sterilization of medical devices, and in particular, to sterilization of medical adhesives.

2. Description of the Related Art

Current treatments for varicose veins can in some cases can carry a high morbidity, be ineffective, and/or be very painful, leaving the patients out of commission for quite some time. A closure system for varicose veins can compose several different components within a kit, each requiring sterilization.

SUMMARY

The closure system kit can be sterilized by using Ethylene Oxide. However, in some cases, this process is not effective for fluids such as medical adhesives in the kit. Therefore, a new process is needed to efficiently sterilize a medical adhesive, such as a cyanoacrylate composition for treating, among other things, venous insufficiency. Proper sterilization of the medical adhesive decreases the risk of infection, allows patients to be back on their feet as soon as possible, as well as having a relatively painless treatment process of varicose veins. A novel system and method for sterilization of medical adhesives is disclosed herein.

The sterilized medical adhesive disclosed herein can be used in a medical device including a syringe filled with the medical adhesive that is systematically introduced into the treated vein via catheter. A dispenser gun is attached to the syringe in order to regulate precisely how much adhesive is dispensed with each pull of the trigger. Prior to use in the medical device, the adhesive is mixed and packaged in, for examples, 4 ml vials. In some embodiments, upon packaging in, for example, the 4 ml vials, the adhesive can be sterilized. In some embodiments, the vials can be 1, 2, 3, 4, 5, 6, 7, 8, 9, 10 ml or larger.

In some embodiments, a method of sterilization is first selected. After the method is selected, proper parameters can be chosen for the specific process in order to produce a sterile product. After establishing a validated sterilization process, lots of medical adhesive can be consistently sterilized in order to achieve first demand. With proper maintenance and monitoring, the process can be used until the loading configuration or specifications of the medical adhesive are changed.

In some embodiments, the medical adhesives can be sterilized before being packaged with the rest of a medical device's components in, for example, a kit. The sterilization process can adhere to American National Standards Institute (ANSI) standards. This process can be executed once to fulfill the first demand and therefore can produce a lot size that accommodates this. This process can also be repeated reliably for multiple orders. The adhesive can then be tested to ensure that it performs to clinical and/or technical standards. The temperatures and durations for sterilization can be varied.

In accordance with embodiments disclosed herein, there is provided a method for sterilizing a medical adhesive. The method comprises enclosing the medical adhesive in a first housing, the first housing configured to seal the medical adhesive. The method further comprises positioning the first housing with the medical adhesive in a tray, the tray configured to secure the first housing in a first predetermined position on the tray. The method further comprises positioning the tray with the first housing on an oven rack, the oven rack inside an oven. The method further comprises operating the oven at a predetermined temperature profile over a time duration to heat the medical adhesive to about the predetermined temperature profile over the time duration sufficient to sterilize the medical adhesive, wherein the predetermined temperature profile includes a temperature range of about 110° C. to about 120° C. and the time duration includes about 2 hours plus a ramp-up time of about 40 minutes, wherein following the sterilization process a post-sterilization viscosity of the medical adhesive is within about 5% of the pre-sterilization viscosity of the medical adhesive. Some embodiments may include one or more of the following features: enclosing a biological indicator in a second housing, the second housing configured to seal the biological indicator, the biological indicator configured to indicate whether sterilization has been achieved; positioning the second housing with the biological indicator in the tray, the tray configured to secure the second housing in a second predetermined position on the tray; wherein the biological indicator is enclosed in the second housing with the medical adhesive, and wherein the medical adhesive substantially surrounds the biological indicator; enclosing the medical adhesive in a first plurality of housings, the first plurality of housings configured to seal the medical adhesive; positioning the first plurality of housings with the medical adhesive in the tray, the tray configured to secure the first plurality of housing in a first plurality of predetermined positions on the tray; wherein the first plurality of housing are heated to substantially a same temperature over the time duration; wherein the first plurality of predetermined positions start at a center of the tray and radiate toward the perimeter as the first plurality of housing are positioned in the tray to help provide the same temperature over the time duration; enclosing a substance not for patient application in a second plurality of housings, the second plurality of housings configured to seal the substance; positioning the second plurality of housings with the substance in the tray, the tray configured to secure the second plurality of housing in a second plurality of predetermined positions on the tray; wherein the second plurality of predetermined positions are substantially at a perimeter of the tray; and/or wherein the medical adhesive comprises a cyanoacrylate.

In accordance with embodiments disclosed herein, there is provided a method for sterilizing a medical adhesive. The method comprises enclosing the medical adhesive in a first housing, the first housing configured to seal the medical adhesive. The method farther comprises positioning the first housing with the medical adhesive in a tray, the tray configured to secure the first housing in a first predetermined position on the tray. The method further comprises positioning the tray with the first housing on an oven rack, the oven rack inside an oven. The method further comprises operating the oven at a predetermined temperature profile over a time duration to heat the medical adhesive to about the predetermined temperature profile over the time duration sufficient to sterilize the medical adhesive, wherein the predetermined temperature profile includes a temperature range of about 110° C. to about 120° C. and the time duration includes about 2 hours.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of any subject matter described herein.

BRIEF DESCRIPTION OF THE DRAWINGS

The foregoing and other features of the present disclosure will become more fully apparent from the following description, taken in conjunction with the accompanying drawings. Understanding that these drawings depict only some embodiments in accordance with the disclosure and are, therefore, not to be considered limiting of its scope, the disclosure will be described with additional specificity and detail through use of the accompanying drawings.

DETAILED DESCRIPTION

Figure 1A:
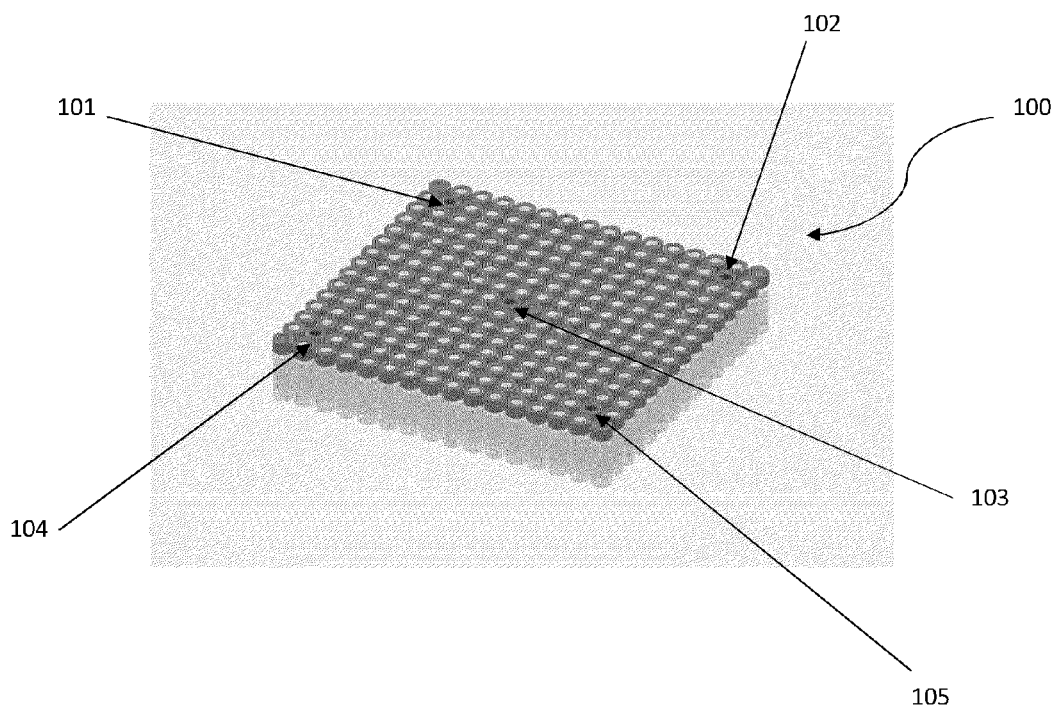
FIG. 1A illustrates an embodiment of a load configuration in a tray.

In the following detailed description, reference is made to the accompanying drawings, which form a part hereof. In the drawings, similar symbols typically identify similar components, unless context dictates otherwise. The illustrative embodiments described in the detailed description and drawings are not meant to be limiting. Other embodiments may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and make part of this disclosure.

The headings provided herein are for convenience only and do not necessarily affect the scope or meaning of the claims.

In some embodiments, a customized sterilization process is designed to be validated per ANSI standards. First, a proper process can be selected to sterilize the product. In some embodiments, dry heat sterilization can be used. In addition to the type of sterilization, a method for determining if the resulting product would be sterile or not can be selected. For this determination, Biological Indicators (BI's) can be used. However, there are many different choices to choose from.

Second, parameters can be evaluated in order to choose the most efficient cycle time. In some embodiments, the cycle time can vary from about 1-8 hours, including about 2-7 hours, including about 1, about 2, about 3, about 4, about 5, about 6, about 7, or about 8 hours, including ranges bordering and the foregoing values. The temperatures can vary from about 100 to about 200° C., including about 100 to about 120° C., including about 110 to about 120° C., including about 110 to about 140° C., including about 120 to about 130° C., including about 120 to about 180° C., including about 140 to about 160° C., including about 100, about 105, about 110, about 115, about 120, about 125, about 130, about 135, about 140, about 145, about 150, about 155, about 160, about 165, about 170, about 175, about 180, about 185, about 190, and about 195° C., including ranges bordering and the foregoing values. The sterilization cycle can be performed in one 8-hour workday, or shorter or longer time periods. Tests can have a Biological Indicator in the oven chamber that can indicate whether the process is adequate for the sterilization of the medical adhesive. The process that uses the least amount of heat for the shortest amount of time and passes a sterility test can be selected in some embodiments. Having a shorter amount of time while passing the sterility test can help achieve patient benefits as discussed herein with minimal costs.

Further, not to be limited by theory, but using the least amount of heat (or temperature) necessary to sterilize the medical adhesive helps prevent curing of the medical adhesive. In certain embodiments, at higher temperatures, a medical adhesive, such as a medical adhesive with cyanoacrylates, can lose viscosity when exposed to higher temperatures. Keeping the sterilization temperatures low, such as, for example, with nominal parameters as discussed herein without requiring a relatively long heating time, helps prevent the loss of viscosity and prevent curing in some medical adhesives. In some embodiments, following sterilization the difference between the viscosity of the adhesive is within about 200 cp, 150 cp, 100 cp, 75 cp, 50 cp, 40 cp, 30 cp, 25 cp, 20 cp, 15 cp, 10 cp, 5 cp, 2 cp, 1 cp, or less compared to the pre-sterilization viscosity of the adhesive. In some embodiments, following sterilization the difference between the viscosity of the adhesive is within about 10%, 9%, 8%, 7%, 6%, 5%, 4%, 3%, 2%, 1%, 0.5%, or less compared to the pre-sterilization viscosity of the adhesive. Further systems and methods for treatment of venous insufficiency and other conditions that can be used or modified for use with sterilization systems and methods as described herein can be found, for example, in U.S. Pub. No. 2010/0217306 A1 to Raabe et al., which is hereby incorporated by reference in its entirety.

Once the process and parameters have been determined, the process can be validated per ANSI standards. ANSI can involve a documented installation qualification, operation qualification and performance qualification. Once all three of those documents are written and performed, the process can be validated and a complete lot of medical adhesive will be able to undergo the sterilization process. In some embodiments, the process described herein can produce the following: (A) One or more sterilized lots of medial adhesive; (B) A validated sterilization process that is capable of being performed in the future; (C) A process that can be executed in one 8-hour workday.

To maintain sterility (prevent recontamination) after the sterilization process, the medical adhesive can be packaged into a sterile barrier, such as, for example, vials prior to sterilization as discussed herein. The sterile barrier can withstand mechanical stresses such as stresses that arise during shipping and handling. In some embodiments, the sterile barriers (e.g., vials) can resist applications of torque ranging from about 4 to about 24 inch-pounds, including about 8 to about 16 inch-pounds, including ranges bordering and the foregoing values. The sterile barrier is able to maintain sterility of the medical adhesive for about one-half to about 2 years, including about 1 year, including ranges bordering and the foregoing values, after sterilization as discussed herein.

Sterilization Processes

Sterilization is the process of killing or removing microorganisms from a product to help ensure that it is sterile. In some embodiments, sterilization may include one, two, or more of dry heat sterilization, moist heat sterilization (steam), sterilization using electromagnetic energy (including, for example, optical, RF, ultrasound, and microwave energy) and/or gas sterilization, e.g., with Ethylene Oxide (ETO). In some embodiments, electromagnetic energy sterilization could precede or follow heat sterilization. Each process may have varying parameters, which can result in highly customizable sterilization solutions for each individual device.

Dry heat sterilization can sterilize small objects and can involve inexpensive equipment. In some embodiments, the parameters include at or about 170° C. for one hour or 140° C. for three hours. The total cycle times can be about twice as long (e.g., two hours or six hours, respectively) due to the ramp up and cool down of the oven and the devices to be subjected to the process.

In some embodiments, there are several advantages when choosing dry heat as the primary mode of sterilizing a device. Dry heat sterilization involves a process that is nontoxic. The setup can be simple to allow for implementing a process that can specialize for a single device in a cost effective manner. Because of these advantages, dry heat is a popular solution for small companies that are interested in low volume production. However, dry heat sterilization can be applied on a large commercial scale. Due to the high temperatures, dry heat should be chosen for objects that can withstand such an environment for an extended period of time. The slow rate of heat penetration and microbial killing may make this a time-consuming method that is not suitable for some materials.

For products that cannot be exposed to long periods of high temperatures, moist heat sterilizations can provide an option that operates at a relatively lower temperature of approximately 121° C., for example. Because there is moisture in the air, the heat is more effective at killing the bacteria present on the device.

Just like dry heat sterilization, moist heat provides a process in which two variables can be controlled: temperature and time. Due to the lower temperature and shorter cycle times, hospitals and other healthcare facilities have steam sterilizers. These sterilizers can be used for quick sterilization of reusable equipment as well as liquids/fluids that are not affected by the heat or moisture.

ETO can provide the ability to sterilize a kit containing many different component, which sets it apart from dry and moist heat. However, instead of having two parameters to regulate, there are four. These include time, temperature, heat, and ETO gas concentration/distribution. Since heat may be not the primary parameter for killing the bacteria, the process works with the penetration of the gas doing the work. This may limit the materials that can be sterilized with ETO because many materials cannot be easily penetrated.

Each of these three processes provides their respective advantages and disadvantages and therefore, may be used in parallel for different components of a medical device.

Biological Indicators

Biological Indicators (Ms) can be used to monitor the efficacy of sterilization processes for medical products. BIs contain high numbers, generally $10^4$ to $10^6$, of bacterial endospores that are highly resistant to the sterilization process for which they are designed for. The spores of bacteria are placed on a vehicle that is used to transport the bacteria through the sterilization process in order to determine the efficiency of the process. In some embodiments, the spores are transported through the sterilization process via a suspension or a solid material such as a strip. BIs are the process indicators that directly monitor the lethality of a given sterilization process, have demonstrated resistance to the sterilization agent, and/or are more resistant than the bioburden found on medical devices.

There are several different kinds of BIs depending on the application and the sterilization process that is to be monitored. Just like sterilization process selection, which BI to select can contribute to the overall effectiveness of the process. Some common types of BIs include spore strips, mini spore strips, spore discs, self contained, spore ampoules, spore suspensions as well as custom spore solutions.

Biological indicators are designed to test worst case scenarios and therefore can be placed in the hardest to reach places within the device. For example, if the device to be sterilized is a solid, hollow piece of plastic, the BI can be placed inside the thickest part of the device to help ensure that it represents the worst case scenario. For this example, a spore strip can be used due to its ability to be secured to the inside of the part and also since it is the cheapest of the available BIs. Discs and mini spore strips may be used when space is an issue and a standard strip will not suffice. Spore ampules and suspensions may be used for monitoring the sterilization of liquids, where a solid BI may absorb too much of the liquid and fall apart.

Once a medium is chosen, there are several species of bacteria available to monitor specific sterilization processes. In some implementations, *bacillus atrophaeus* may be used to monitor dry heat and ETO while *geobacillus stearothermophilus* may be used for steam. Along with species, each BI can be tailored to operate within a temperature range and can be researched before selecting the one to monitor the sterilization process.

Due to having living bacteria within the BIs, BIs should be handled with care and properly stored. In some embodiments, before use, they may be stored between about 0 to about 10° C., including about 2 to about 8° C., including about 1, about 2, about 3, about 4, about 5, about 6, about 7, about 8, and about 9° C., including ranges bordering and the foregoing values. After the BIs are subjected to the sterilization cycle, they can be sent to a lab to undergo testing for bacterial growth. This involves an incubation period ranging from, about 1 to about 10 days, including about 2 to about 7 days, including ranges bordering and the foregoing values, depending on the exact product used. After incubation, the BIs are compared to the negatives/controls provided from the manufacturer to check for growth. Generally, a color change is triggered by bacterial growth and therefore can represent a failed sterilization process.

Validation of Sterilization Processes

Once an appropriate sterilization process is selected along with a suitable type of BI, the sterilization process can be validated. Once validated, the process is deemed sufficient at sterilizing the products subjected to it and may be repeatable indefinitely when monitored properly. There are several components to the validation to help ensure all aspects of the process are regulated and operating per the manufacturer's instructions. The three main sections are the Installation Qualification (IQ), the Operation Qualification (OQ), and the Performance Qualification (PQ).

IQ can help ensure that all equipment is installed as specified within the user's manual. This can include utilities such as water, electrical, steam, and air. Also involved is the overall construction and connections of the equipment to be used. All piping and wiring can be carefully inspected for discontinuities that could negatively affect the performance of the equipment. Pre-determined construction and installation parameters can be assessed once installation permits are obtained.

Once the equipment has been inspected and documented, OQ can help ensure that it is operating correctly. OQ can include testing the equipment over its pre-defined and installed operating range to verify consistent performance. This can include all controls, alarms, and monitoring devices. OQ can include monitoring and documenting how the chamber heats up and is distributed throughout it. Reproducible heating throughout the chamber can be demonstrated by performing three empty chamber cycles.

Once the equipment has been installed and is operating correctly, performance qualification can be performed. PQ can represent actual lots undergoing the sterilization process that are tested for bacterial growth. Four total cycles are to be completed in some embodiments. Three of these cycles are half cycles and the last is a full cycle. The reasoning for the half cycles comes from the overkill method. If a half cycle test properly sterilizes the product, then it is with much more certainty that a full cycle will substantially eliminate of bacterial growth. The half cycles can be performed at the minimum, nominal, and maximum parameter settings. Therefore, the machine can be validated to run within a window, making the target parameters easier to control and regulate.

The cycles can be tested using a full load of medical adhesive as well as BIs distributed throughout. Once the four cycles are done, the BIs can be checked for bacterial growth. Every single BI that is subjected to the sterilization process should produce a negative result when tested for bacterial growth in order for PQ to be considered complete.

Once the IQ, OQ, and PQ are completed the process is considered to be validated. All documentation and results can be presented in a comprehensive report that explains in detail the steps taken as well as the results that were observed for each necessary parameter.

Design

Overall, the end result can be a sterilized lot of medical adhesive. In order to achieve this, a sterilization process can be validated per ANSI standards. The sterilization process can be executed once to produce the lot for first demand. However, if need be, all of the documentation and instructions will be in place to execute the sterilization process when needed.

The sterilization process is designed in a manner that can use used with standard parts purchased from online retailers to keep cost at a minimum. Another way of keeping costs low is having the ability to execute the process within, e.g., the duration of one 8-hour work day.

Sterilization Arrangement

The following example provides certain embodiments of procedures related to sterilization of medical adhesives and other compositions. As will be understood, these examples are illustrative, and the parameters, equipment, and procedures used can be varied in a myriad of ways depending on the specific application.

The first step in the sterilization of the medical adhesive can be choosing the means of sterilization. In some embodiments, ETO is not used in certain circumstances due to the fact that it might not penetrate the glass vials in an efficient manner. That leaves both steam and dry heat as potential candidates in some embodiments.

The medical adhesive itself can be highly reactive to water and plasma by design. This can causes concern with the steam method of sterilization. If any steam penetrates the vial's septum or if there is a small amount of adhesive leaking out, the entire bottle's adhesive can cure while in the steam oven. Therefore, in some embodiments, dry heat can be selected. While temperatures for dry heat processes can be higher than for steam processes, dry heat processes reduce the risk of adhesive curing. In some embodiments, a convection oven can be used, such as, for example, a Blue M 146 series convection oven available on the market.

To determine the effectiveness of the sterilization process, biological indicators (BI) can be utilized in most or every cycle of the process qualification. In some embodiments, the BI include PT-1150, SGM Biotech Steril Amp II 5230. This is a self-contained ampoule with a population of $10^6$ of temperature resistant bacteria, *Bacillus Subtilis*. It is designed to work (be tested) within, e.g., 110-118° C., which can be used in sterilization parameters of, for example, 115±5° C. PT-1150, SGM. The placement of the BIs can be in the most difficult to sterilize location, which is in the center of the vial. The vial size is 50 mm (height) by 15 mm (diameter). The BI size is 26 mm (height) by 6.5 mm (diameter). When placed inside the vial, the BI can be completely submerged and surrounded by the product that is being sterilized.

Sterilization Example

The following example provides certain embodiments of procedures related to sterilization of medical adhesives and other compositions. As will be understood, these examples are illustrative, and the parameters, equipment, and procedures used can be varied in a myriad of ways depending on the specific application.

In some embodiments, Blue M 146 Series convection oven is used to sterilize medical adhesive in 6 ml vials. The vials can be arranged as indicated in FIG. 1A. FIG. 1A illustrates an embodiment of a load configuration in a tray 100 that can be placed on a baking sheet. In some embodiments, two or more trays 100 are placed into the convection oven.

The BIs are placed in a number of vials, such as 11 vials. The BI's can be completely submerged in medical adhesive. Five of the BI vials are loaded in a configuration on a first tray 100 as illustrated in FIG. 1A with reference numbers 101, 102, 103, 104, and 105 indicating an example configuration. The other five BI vials are loaded in a same configuration on a second tray 100 as illustrated in FIG. 1A with reference numbers 101, 102, 103, 104, and 105 indicating an example configuration, same as for the first tray 100. It is understood that other load configurations of the vials on the tray are possible to sterilize or validate the sterilization process as discussed herein. In some embodiments, the first and the second trays can have load configurations that are different from each other. The 10 vials can be labeled for reference. The eleventh vial is the control and is not placed in the oven (not loaded in the tray). All BIs, including the control, can come from the same lot of BIs. If multiple BI lots are used, then 1 control BI & vial sample can be submitted for testing for each BI lot. If there are not enough vials in the lot to complete the load, appropriate dunnage vials as discussed herein can be used to fill the tray. Dunnage vials may be filled with, for example, tap water or medical adhesive. The dunnage vials can be full in some embodiments. The first and second tray 100 are placed on, for example, the 2nd and 4th shelves (from the top) in the oven with complete loads as illustrated in FIG. 1A.

The tray(s) 100 with the vials are placed into the oven. The oven is turned on for the temperatures and durations as discussed herein for sterilization (e.g., full cycle at nominal parameters including about a generally linear, accelerating, or decelerating 10, 20, 30, 40, 50, or 60 minute ramp up to 115±5° C. for a 2 hour sterilization period and removal within about 30, 20, 15, 10 minutes, or less after sterilization). After completion of the sterilization cycle, the vials are cooled to 35° C. or less. In some embodiments, the BI vials are not be refrigerated. The 11 BI vials (10 test units, 1 control) can be submitted for 3rd party testing.

Another Sterilization Example

The following example provides certain embodiments of procedures related to sterilization of medical adhesives and other compositions. As will be understood, these examples are illustrative, and the parameters, equipment, and procedures used can be varied in a myriad of ways depending on the specific application.

Figure 1B:
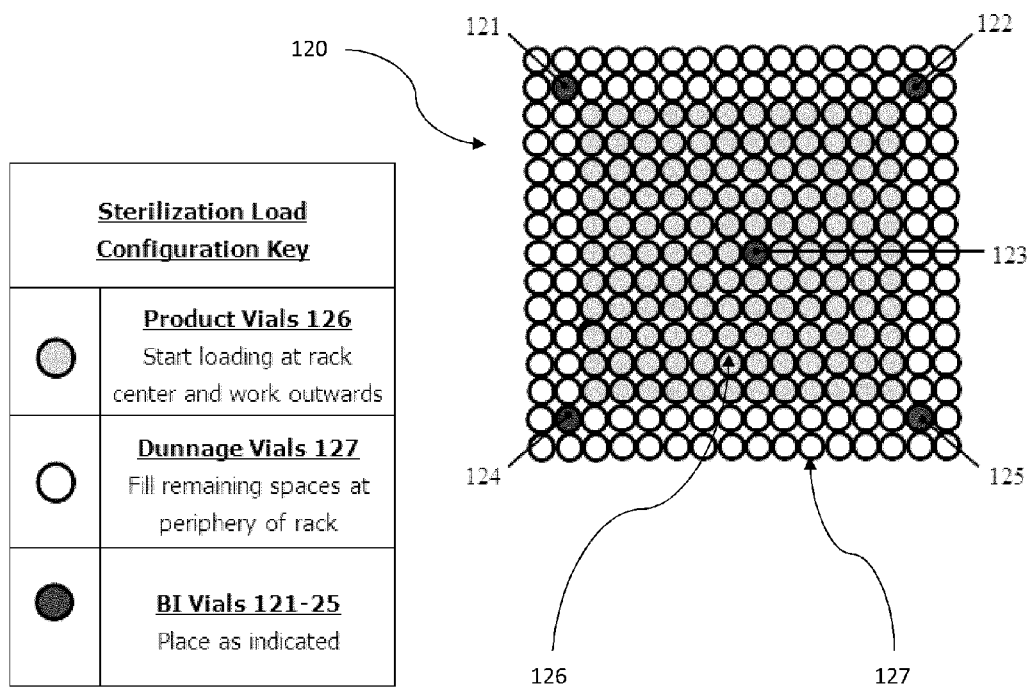
FIG. 1B illustrates an embodiment of a load configuration in a tray.

In some embodiments, a Blue M 146 Series convection oven is used to sterilize medical adhesive in 6 ml vials. The vials can be arranged as indicated in FIG. 1B. FIG. 1B illustrates an embodiment of a load configuration in a tray 120 that can be placed on a baking sheet. In some embodiments, two or more trays 120 are placed into the convection oven.

Eleven (or more or less) product vials are selected randomly from the sterilization load to make BI vials. BI is inserted into each BI vial using cleaned tweezers. The BIs are fully submerged in the adhesive. Ten of the BI vials are numbered from 1-10 on the cap and vial using, for example, a permanent marker, and the remaining vial is labeled with a 'C' as a control sample. All BIs, including the control, can come from the same lot of BIs. When multiple BI lots are used, then 1 control BI vial can be submitted for testing for each BI lot.

Five of the BI vials are loaded in a configuration on a first tray 120 as illustrated in FIG. 1B with reference numbers 121, 122, 123, 124, and 125 indicating an example configuration. The other five BI vials are loaded in a same configuration on a second tray 120 as illustrated in FIG. 1B with reference numbers 121, 122, 123, 124, and 125 indicating an example configuration, same as for the first tray 120. Product vials 126 are loaded the tray 120 as illustrated in FIG. 1B starting from the center working outwards. It is understood that other load configurations of the vials on the tray are possible to sterilize or validate the sterilization process as discussed herein. In some embodiments, the first and the second trays can have load configurations that are different from each other. The eleventh vial is the control and does not go in the oven. When there is vial space remaining in the tray 120 after loading the product vials 126, dunnage vials 127 can be used to fill the tray at the periphery as illustrated in FIG. 1B. Dunnage vials 127 may be filled with, for example, tap water or medical adhesive. The dunnage vials 127 can be full in some embodiments. The product vials 127 and dunnage vials 127 are inspected to help ensure the vial and cap are crack free and that the vial is filled to the appropriate level. The first and second trays 120 are placed on, for example, the top and bottom shelves (from the top) in the oven with complete loads as illustrated in FIG. 1B.

The outer two perimeter rows on each rack are not used for product and filled with dunnage vials 127. In some embodiments, the outer 1, 2, 3, 4, 5, or more perimeter rows on each are not used for product and filled with dunnage vials 127. The vials in or near the outer perimeter of the tray 120 can be subjected to higher and lower temperature extremes in the oven than the vials toward the center of the tray 120. Keeping the product vial 126 toward the center of the tray 120 helps ensure that substantially all or most of the product vials 126 are exposed to about the same temperature.

The tray(s) 120 with the vials are placed into the oven. The oven is turned on for the temperatures and durations as discussed herein for sterilization (e.g., full cycle at nominal parameters including about a generally linear, accelerating, or decelerating 10, 20, 30, 40, 50, or 60 minute ramp up to 115±5° C. for a 2 hour sterilization period and removal within about 30, 20, 15, 10 minutes, or less after sterilization). After completion of the sterilization cycle, the vials are cooled to 35° C. or less. In some embodiments, the BI vials are not be refrigerated. The 11 BI vials (10 test units, 1 control) can be submitted for 3rd party testing. Three percent (3%) of the lot's product vials 126 can be randomly selected (up to 10) and submitted to a 3rd party lab, for example, for pyrogen testing using a limulus amebocyte lysate (LAL) assay.

Engineering Protocol

An Engineering Protocol can include a validation plan for the dry heat sterilization of an adhesive. The Engineering Protocol can include components of the validation process and the reasoning for each step. The parameters can be chosen through experimentation. Once the parameters are chosen, they can be used for every cycle after the validation is complete. In order to use different parameters on an official, released lot, the new parameters can be validated through a separate validation plan. Additionally, a unique configuration of, for example, 192 vials, can be used each time. The configuration can contain all 192 vials or less in order to adhere to the validated process. In implementations where the desired lot is too small to fill out the configuration, "dummy" (or dunnage) vials can be used to complete the configuration. These "dummy" vials can be the exact size and shape of the actual vials and filled with an R&D lot of the adhesive or some other substance such as water. This can help ensure that the whole configuration heats and cools as demonstrated within the process qualification.

The process qualification can utilize the overkill method, for example, in order to validate the dry heat sterilization process. The overkill method tests the half cycles of the process to ensure that the full cycle can produce repeatable sterility as discussed herein. Three half cycles can be performed at the nominal, minimum, and maximum parameters. One full cycle can be performed at the nominal parameters. If these tests can exhibit zero or substantially zero bacterial growth, they can become a validated process. If specifications within the Installation and Operation Qualification (IOQ) and PQ are met or exceeded, the validation can be completed.

Example Engineering Protocol

The following example provides certain embodiments of procedures related to sterilization of medical adhesives and other compositions. As will be understood, these examples are illustrative, and the parameters, equipment, and procedures used can be varied in a myriad of ways depending on the specific application.

In some embodiments, the Engineering Protocol is used to validate the dry heat sterilization process for medical adhesives. This sterilization validation protocol can be executed to support sterility claims. The parameters that control the sterilization process are exposure time and temperature.

Figure 1C:
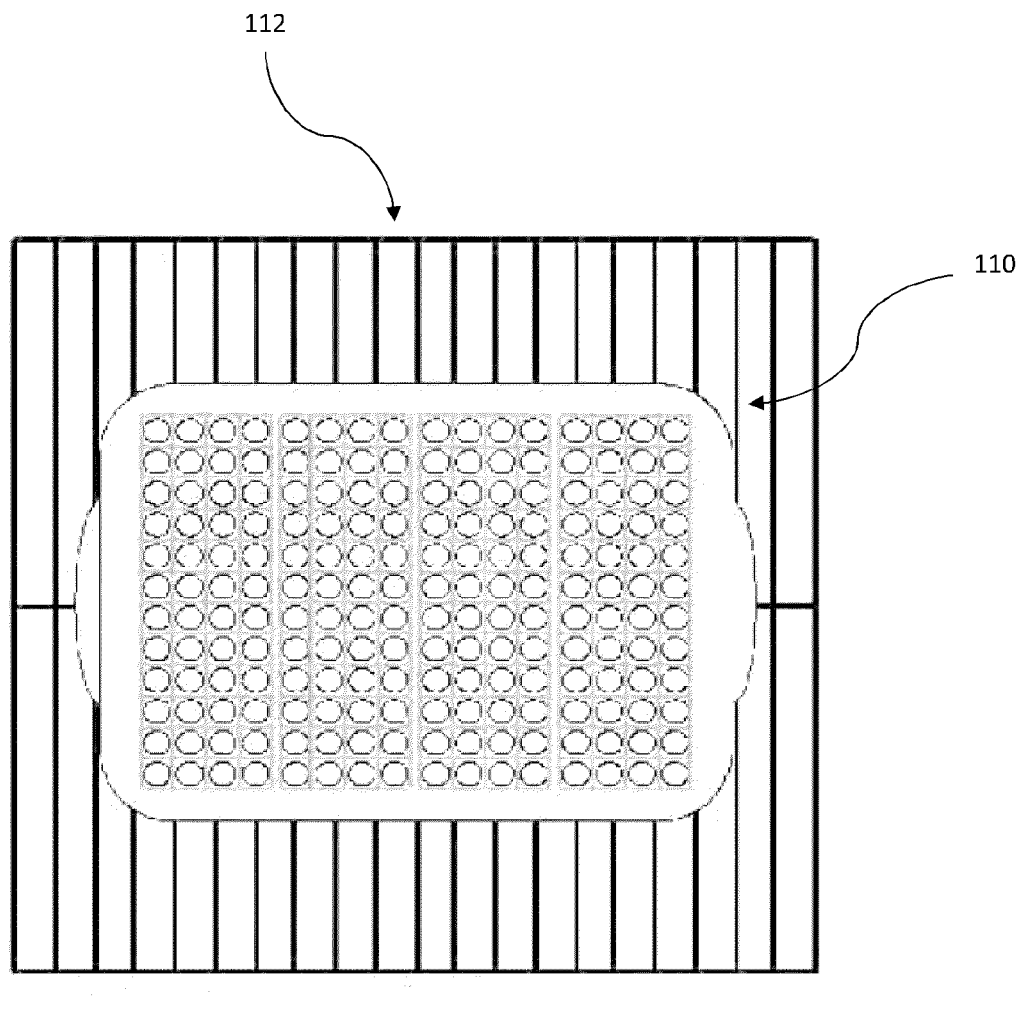
FIG. 1C illustrates an embodiment of a load configuration in a tray.

The parameters validated for the dry heat sterilization process of medical adhesive is 115° C.±5° for 4-4.5 hours. The configuration validated is a 192 vial configuration. This is the exact configuration that some product lots can use. Dunnage vials are used to complete the load when lot sizes are smaller than the load configuration. FIG. 1C illustrates an embodiment of a load configuration in a tray 110 placed on a baking sheet 112 that can be placed into an oven.

The sterilization oven used is a Blue M Forced Convection Oven. The installation/operational qualification verifies that the oven functions within the parameters of the sterilization process. This includes verifying the oven operation consistency, temperature monitoring accuracy, and alarm function. The process qualification utilizes the overkill method in order to validate the dry heat sterilization process. The overkill method tests the half cycles of the process to ensure that the full cycle will produce repeatable sterility. Three half cycles are performed at the nominal, minimum, and maximum parameters. One full cycle is performed at the nominal parameters.

The dunnage vials can include various R&D (medical) adhesive formulations. All of the different formulations replicate the thermal properties of the various adhesives and therefore can be used to represent adhesives used in the marketplace. Additionally, in some embodiments, these properties are not affected by repeatedly being heated up and cooled down and therefore can be used until the vials show physical flaws.

To determine the effectiveness of the sterilization process, biological indicators (BI) are utilized in every cycle of the process qualification. The BI utilized is PT-1150, SGM Biotech Steril Amp II 5230 which is a self-contained ampoule with a population of $10^6$ of temperature resistant bacteria, *Bacillus Subtilis*. The BI is designed to work (be tested) within 110-118° C., which is consistent with sterilization parameters of, for example, 115±5° C. The placement of the BIs can be in the most difficult to sterilize locations, which is in the center of the vial. The vial size is 50 mm (height) by 15 mm (diameter). The BI size is 25 mm (height) by 6.5 mm (diameter). When placed inside the vial, the BI is completely submerged and surrounded by the product that is being sterilized.

Each qualification test can meet the specifications as referenced in each respective document. Both the IOQ and the PQ can be completed in order for the sterilization process to be validated. Any units not used for testing from the sterilization validation lots can be released for clinical use, provided that full traceability is maintained and the sterilization validation results are as expected.

Bioburden is established and documented to ensure that the numbers and resistance of bioburden are within the allowable range for the parameters being used. For small batch sterilization of less than 10 cubic feet, a minimum of BIs are used. Twelve BIs and an additional negative BI are distributed throughout the load. For small batch sterilizations of less than 10 cubic feet, three temperature sensors are used. In some embodiments, six temperature sensors are used to ensure the uniformity of the chamber (less than 4 cubic feet).

IOQ can demonstrate that the equipment has been installed according to the manufacturer's specifications and that the equipment operates according to design specifications for performance, control system function, and data collection systems associated with the equipment. The physical portion of the PQ can demonstrate that the sterilization process is reproducible over the range of conditions proposed for routine processing. The microbiological portion of the PQ can demonstrate that the sterilization process consistently achieves sterility of $10^{-6}$ over the range of conditions proposed for routine processing.

Installation and Operation Qualification

The Installation and Operation Qualification (IOQ) can be used to provide documented evidence that the equipment involved has been correctly installed and operating per the manufactures specifications. As discussed herein, in some embodiments, the piece of equipment used for the sterilization process is a Blue M Oven.

In some embodiments, the first step can be ensuring that the equipment was properly labeled and all appropriate documents present. This can include both tags from the manufacturer as well as from an adhesive designer. This checks to make sure that the equipment is properly accounted for within the quality system and therefore can be subjected to all of the appropriate documentation. Included in the IOQ can be a preventative maintenance schedule that can be kept up to date for the duration of the equipment being used. Since the oven can be used for a process that will be validated, a "No Calibration Required" sticker can also be present.

Once all of the paperwork had been taken care of, the oven can be installed. Installation can start at the source of power. A Digital Multi Meter (DMM) can be used to check that the proper voltage is being provided for the unit. In some embodiments, once checked, the oven may not be moved and/or used for production without a new IOQ being executed. An initial visual inspection of all electrical components can also ensure that the oven will be safely operating from the start. After the IOQ, preventative maintenance can monitor this.

After the oven has been installed in its permanent location, it can be proved that it is performing as per the specifications detailed in the owner's manual. The first step can be powering the unit on and bringing the oven up to a temperature. Next, it can be verified that the oven properly shuts off when it experiences power loss (pull out the plug). Once plugged back in, it may resume heating. Similar tests can be run to verify that the alarm system is in working condition.

Figure 2:
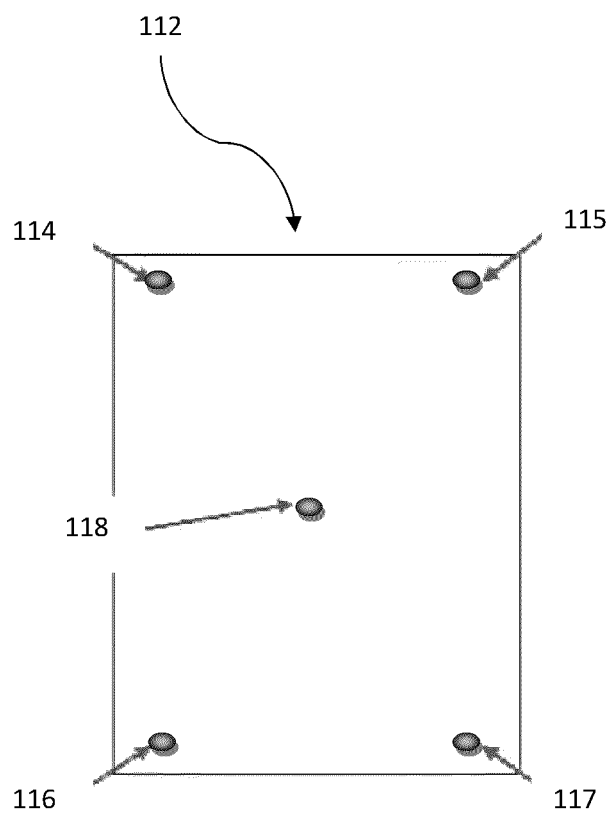
FIG. 2 illustrates an embodiment for placement of thermocouples on a baking sheet.

An oven should be consistent in its performance. The oven can be mapped to verify that the heating is consistent throughout the chamber. To do this, five (or more or less) thermocouples can be placed throughout the chamber and tested on three different levels. The oven can demonstrate even heating to pass inspection. FIG. 2 illustrates an embodiment for placement of thermocouples on a baking sheet and/or oven rack 112 to measure a temperature gradient of the oven. Five thermocouples are located on the baking sheet 112 as indicated by reference numbers 114, 115, 116, 117, and 118 in FIG. 2. The IOQ document can be completed and filed with quality assurance before moving on to the parameter testing.

Parameter Testing

In order to determine the appropriate parameters for the sterilization process, several tests can be completed to help verify the acceptability of each option. In some embodiments, the variables include time exposed to the heat and temperature of the oven. Half cycles durations of 2, 3 and 4 hours can be used with temperatures of, for example, 120 and 130° C. Half cycle times can be used in order to exercise the overkill method as discussed herein. In some embodiments, the cycle time can vary from about 1-8 hours, including about 2-7 hours, including about 1, about 2, about 3, about 4, about 5, about 6, about 7, or about 8 hours, including ranges bordering and the foregoing values. The temperatures can vary from about 100 to about 200° C., including about 100 to about 120° C., including about 110 to about 120° C., including about 110 to about 140° C., including about 120 to about 130° C., including about 120 to about 180° C., including about 140 to about 160° C., including about 100, about 105, about 110, about 115, about 120, about 125, about 130, about 135, about 140, about 145, about 150, about 155, about 160, about 165, about 170, about 175, about 180, about 185, about 190, and about 195° C., including ranges bordering and the foregoing.

Throughout the duration of the parameter testing, six biological indicators can be used, one for each combination of parameters. Twelve vials filled with the medical adhesive can be used in testing. One vial may have a biological indicator placed within it; another may have a thermocouple placed within it through a slit in the septum. The testing can be done in random order and the oven may be allowed to completely cool in between tests to help ensure accuracy.

After test runs are completed, the self-contained biological indicators as well as a negative control can be sent to a laboratory such as, for example, Micromed Laboratories, to undergo resistance performance testing. The BI's can be incubated at, for example, about 40 to about 70° C., including about 55 to about 60° C., including ranges bordering and the foregoing values, for about 1 to about 10 days, including about 2 to about 7 days, including 48 hours, including ranges bordering and the foregoing values. If the samples show no or substantially no bacterial growth, the tested parameters may be acceptable to move forward with. The shortest cycle time at the lowest possible temperature can be selected reduce degradation and costs as well as adhesive curing as discussed herein. Additional tests may be performed to pursue optimal parameters.

A test can include two runs at 110° C. for 2 hours. The same procedure may be followed as the previous tests and produce similar results. In some embodiments, the cycle time can be 2 hours at a minimum temperature of 110° C.

Process Qualification/Validation

A Process Qualification (PQ) can provide instructions for the process qualification of the dry heat sterilization of the medical adhesive. PQ can outline the details of the three half cycle tests as well as the one full cycle test that will validate the process per the ANSI standard.

Each test can include a full 192 vial configuration with 12 BI's within vials. The configuration can be placed, for example, in the middle of the third rack from the bottom of the Blue M 146 series convection oven. The three half cycles can use "dummy" vials to fill out the configuration, while the full cycle can use actual adhesive. Therefore, if all tests pass, the resultant may not only be a validated process, but also a sterilized lot of medical adhesive.

As an example, a minimum half cycle can be performed at 110° C., followed by a nominal and maximum half cycle at, for example, 120 and 130° respectively. Then a full 4 hour cycle at the nominal temperature can be executed. For the duration of these tests, once the oven gets up to temperature, it can remain within 5 degrees of the desired temperature to be valid.

Throughout the test, readings from the six thermocouples placed in vials within the configuration can be recorded. Once completed, the BI's can be dropped off at a laboratory as discussed herein for testing. In order for the process to be validated, all 48 BIs should show zero or substantially zero signs of bacterial growth after incubation.

Example Process Qualification Procedure

The following example provides certain embodiments of procedures related to sterilization of medical adhesives and other compositions. As will be understood, these examples are illustrative, and the parameters, equipment, and procedures used can be varied in a myriad of ways depending on the specific application.

In some embodiments, the PQ uses the overkill method to validate the dry heat sterilization process. By testing three batches at the half cycles, it can be determined that the full cycle will produce a sterile product consistently. In some embodiments, the BIs can be stored in the refrigerator. Prior to testing, the BI's can be brought to room temperature before being exposed to the sterilization cycle.

Figure 3:
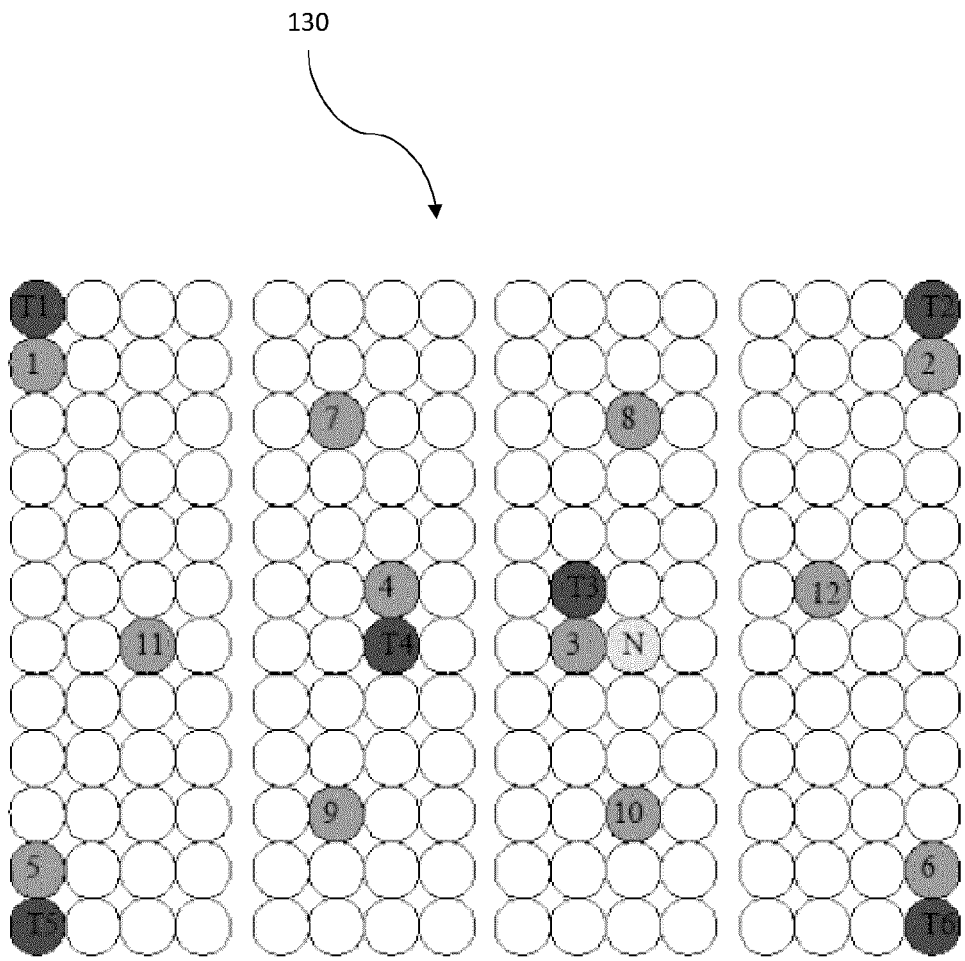
FIG. 3 illustrates an embodiment of a load configuration in a tray.
Figure 6:
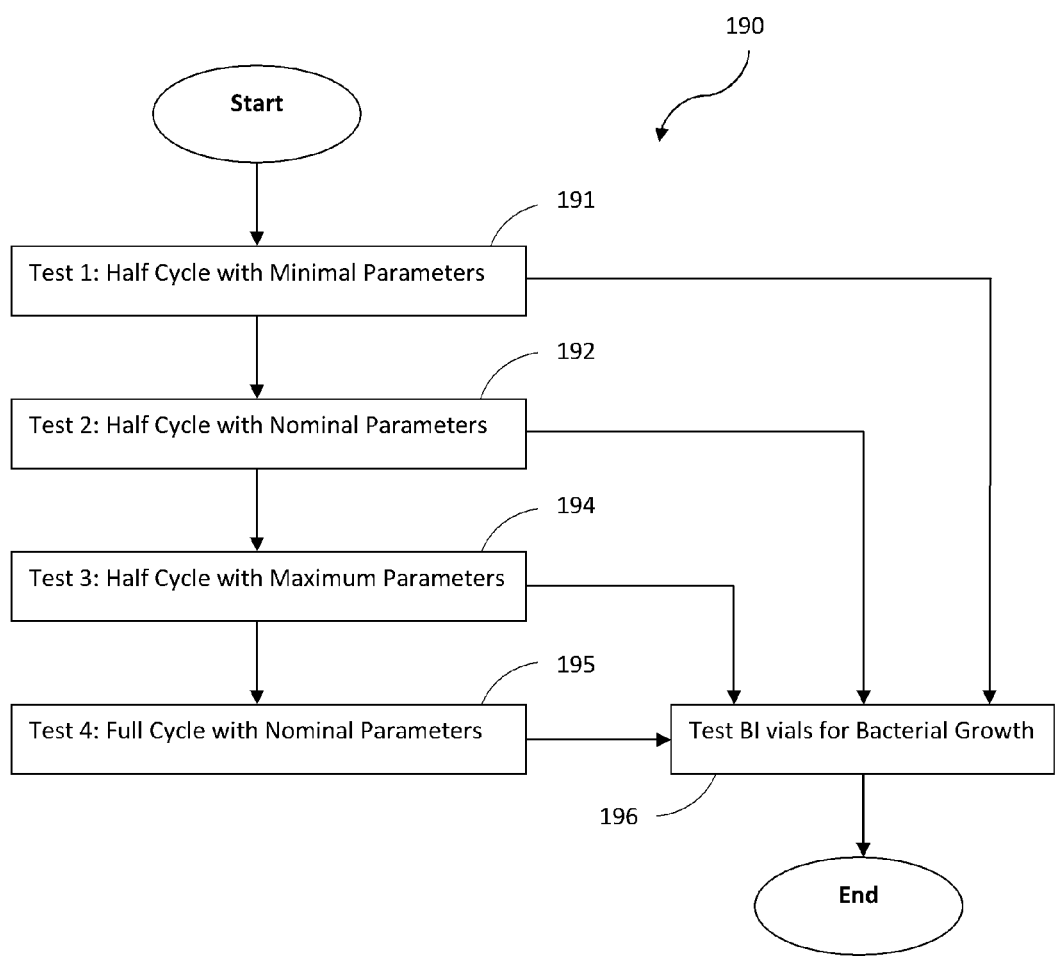
FIG. 6 illustrates a process flow diagram of an embodiment of a process qualification procedure.

FIG. 6 illustrates a process flow diagram of an embodiment of a process qualification procedure 190. In some embodiments, minimum parameter testing for 2 hours (half cycle) 191 includes the following. The oven is turned on to 110° C. and the alarm is set to 120° C. A 192 vial load configuration is arranged in a tray 130 as illustrated in FIG. 3. FIG. 3 illustrates an embodiment of a load configuration in a tray 130. Nineteen vials are filled with a first medical adhesive. 173 dunnage vials are filled with a second medical adhesive that can be the same, similar, or different from the first medical adhesive. Six thermocouples are arranged on the tray 130 as illustrated in FIG. 3 as T1, T2, T3, T4, T5, and T6 indicating an example configuration. It is understood that other thermocouple arrangements and configurations on the tray 130 are possible to measure or sample the temperature of the vials during sterilization. The thermocouples can placed into the vials by slicing a slit into the septum of the vials with a razor blade and sliding the thermocouples into the vials through the slit in the septum. BI vials are loaded on the tray 130 as illustrated in FIG. 3 with reference number 1, 2, 3, 4, 5, 6, 7, 8, 9, 10, 11, and 12 indicating an example configuration. A negative control BI is loaded on the tray 130 as illustrated in FIG. 3 with reference N indicating an example configuration. It is understood that other load configurations of the vials on the tray 130 are possible to qualify or validate the sterilization process as discussed herein. The vials can be labeled to indicate the various vials loaded in the tray 130 as discussed herein. When the oven temperature has reached the sterilization temperature, the baking sheet and tray are placed onto the third rack from the bottom of the oven and slid back until the baking sheet is in the middle of the oven. In some embodiments, the tray is placed into the oven during warm up to the sterilization temperature. Each thermocouple is connected to a thermometer. Observations can be recorded every 15 minutes for 2 hours. The vials can remain at 110±5° C. once the temperature has been reached. Once the cycle is complete, the vials are allowed to return to room temperature. In some embodiments, once at room temperature, the BI-containing vials can be stored in a refrigerator until sent to a lab for analysis 196.

In some embodiments, nominal parameter testing for 2 hours (half cycle) 192 includes the following. The oven is turned on to 115° C. and the alarm is set to 125° C. The same procedures as discussed above for minimum parameter testing can be followed. The vials can remain at 115±5° C. once the temperature has been reached. In some embodiments, once at room temperature, the BI-containing vials can be stored in a refrigerator until sent to a lab for analysis 196.

In some embodiments, maximum parameter testing for 2 hours (half cycle) 194 includes the following. The oven is turned on to 120° C. and the alarm is set to 130° C. The same procedures as discussed above for minimum parameter testing can be followed. The vials can remain at 120±5° C. once the temperature has been reached. In some embodiments, once at room temperature, the BI-containing vials can be stored in a refrigerator until sent to a lab for analysis 196.

In some embodiments, full cycle at nominal parameters for 4 hours 195 includes the following. The oven is turned on to 115° C. and the alarm is set to 125° C. A 192 vial load configuration is arranged in a tray 130 as illustrated in FIG. 3. All vials can be filled with medical adhesive. No dunnage vials are used. Six thermocouples are arranged on the tray 130 as illustrated in FIG. 3 as T1, T2, T3, T4, T5, and T6 indicating an example configuration. It is understood that other thermocouple arrangements and configurations on the tray 130 are possible to measure or sample the temperature of the vials during sterilization. The thermocouples can placed into the vials by slicing a slit into the septum of the vials with a razor blade and sliding the thermocouples into the vials through the slit in the septum. BI vials are loaded on the tray 130 as illustrated in FIG. 3 with reference number 1, 2, 3, 4, 5, 6, 7, 8, 9, 10, 11, and 12 indicating an example configuration. A negative control BI is loaded on the tray 130 as illustrated in FIG. 3 with reference N indicating an example configuration. It is understood that other load configurations of the vials on the tray are possible to qualify or validate the sterilization process as discussed herein. The vials can be labeled to indicate the various vials loaded in the tray 130 as discussed herein. When the oven temperature has reached the sterilization temperature, the baking sheet and tray are placed onto the third rack from the bottom of the oven and slid back until the baking sheet is in the middle of the oven. In some embodiments, the tray is placed into the oven during warm up to the sterilization temperature. Each thermocouple is connected to a thermometer. Observations can be recorded every 15 minutes for 4 hours. The vials can remain at 115±5° C. once the temperature has been reached. Once the cycle is complete, the vials are allowed to return to room temperature. Once at room temperature, the BI-containing vials can packaged in such a way as to help ensure the vials remain upright for delivery to a lab for analysis to check for no or substantially no bacterial growth 196.

Another Example Process Qualification Procedure

The following example provides certain embodiments of procedures related to sterilization of medical adhesives and other compositions. As will be understood, these examples are illustrative, and the parameters, equipment, and procedures used can be varied in a myriad of ways depending on the specific application.

Sterilization of a medical adhesive is accomplished using a low temperature dry heat process. It has been found that sterilization of the adhesive at 115±5° C. does not significantly degrade the product and has previously been validated with a process differing in the overall mass of product sterilized and time of sterilization. FIG. 6 is a process flow diagram of an embodiment of a process qualification procedure 190.

Figure 4:
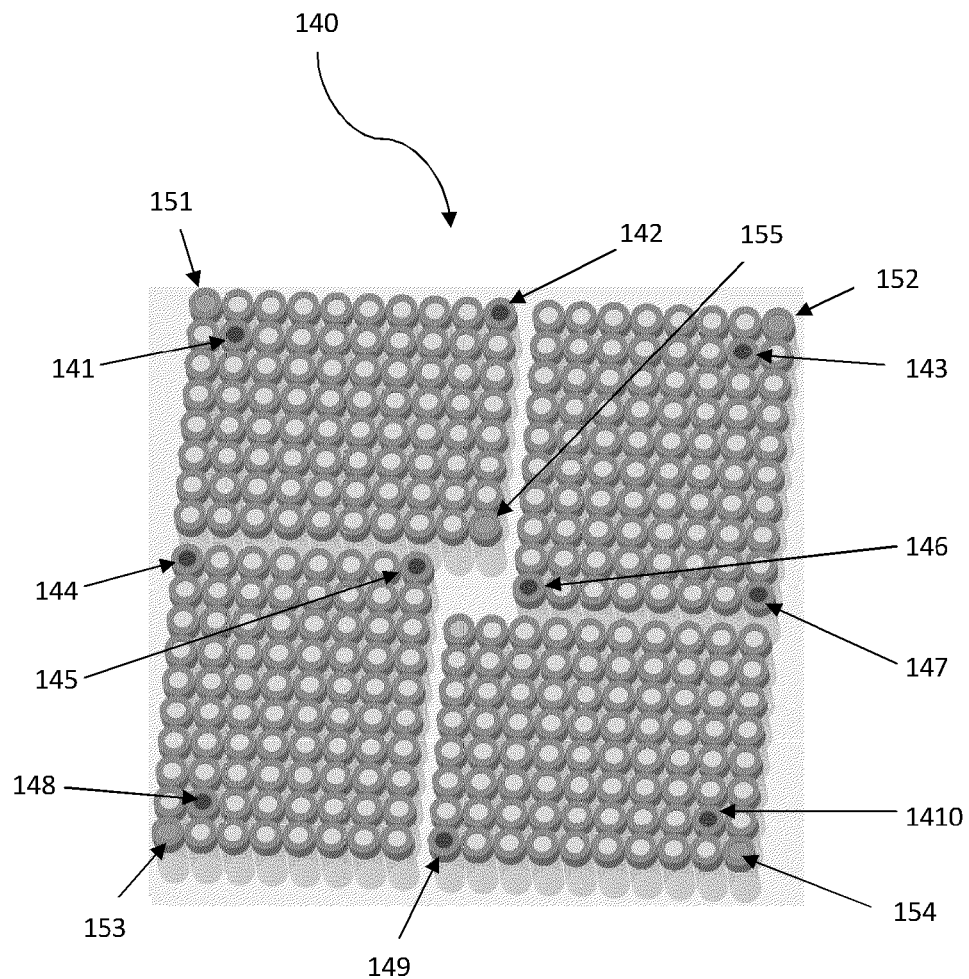
FIG. 4 illustrates an embodiment of a load configuration in a tray with one type of biological indicator.

In some embodiments, the qualification procedure 190 uses the overkill method to validate the sterilization process at the required temperature for a sterilization time of 2 hours. The adhesive is packaged in 6 ml vials with 320 units placed in a ventilated tray 140 as illustrated in FIG. 4. Example biological indicators (BIs) for qualification testing include Raven 1-6100TT and 3-6100TT. By using the overkill method to test three batches at the half cycle (min, nominal, max for 1 hour), it can be determined that the full cycle can consistently produce sterile product.

The following tests are conducted: (A) One test 320 6 ml vials for 1 hour at minimum conditions 191 with Raven 1-6100TT; (B) One test of 320 6 ml vials for 1 hour at nominal conditions 192 with Raven 1-6100TT and Raven 3-6100T; (C) One test of 320 6 ml vials for 1 hour at maximum conditions 194 with Raven 1-6100TT; (D) One test of 320 6 ml vials for 2 hours at nominal conditions 195 with Raven 1-6100TT and Raven 3-6100T.

FIG. 4 illustrates an embodiment of a load configuration in a tray 140 with a single BI type. 321 vials total are placed in the tray 140 on the 3rd shelf from the bottom of the Blue M Oven including: (A) 10 vials are filled with medical adhesive and BIs and loaded in a configuration as illustrated in FIG. 4 with reference numbers 141, 142, 143, 144, 145, 146, 147, 148, 149, and 1410 indicating an example configuration; (B) 1 vial is filled with medical adhesive and a BI placed inside to be a control—this vial does not go in the oven but is sent for testing with the above 10 BI vials; (C) 5 vials are filled with TEC (triethyl citrate) with holes drilled in the caps for thermocouple placement and loaded in a configuration as illustrated in FIG. 4 with reference number 151, 152, 153, 154, and 155 indicating an example configuration; (D) dunnage vials are filled with water.

Ten BI samples are placed in the sterilization tray 140 as shown in FIG. 4. Additionally, one control BI from the same lot as the previous 10 BIs is used as a control. Five thermocouples are used to monitor temperature at the four corners and the center of the sterilization tray 140. Water can be a viable substitute for the adhesive in the dunnage vials because water can have a higher heat capacity than some medical adhesives. TEC is used in the vials containing thermocouples because it has a 300° C. (testing runs at 125° C. max) boiling point to reduce blowing by thermocouple-to-vial seals at sterilization temperature.

Figure 5:
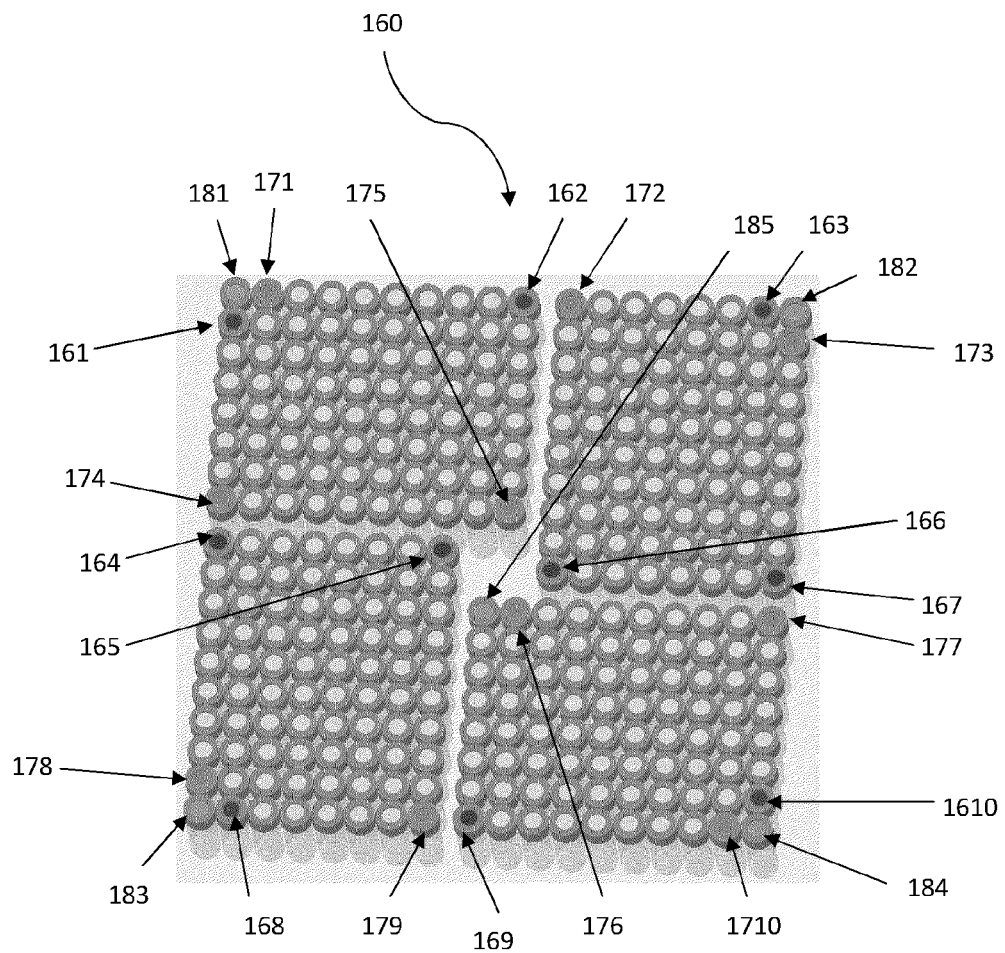
FIG. 5 illustrates an embodiment of a load configuration in a tray with two types of biological indicators.

FIG. 5 illustrates an embodiment of a load configuration in a tray 160 with two BI types. Using two types biological indicators (BI) can help increase validation/qualification efficacy and test for sterilization effectiveness for possible various types of bacterial growth. In some embodiments, more than two, including three, four, five or more BIs may be used to help increase validation/qualification efficacy and test for sterilization effectiveness for possible various types of bacterial growth. 322 vials total are placed in the tray 160 on the 3rd shelf from the bottom of the Blue M Oven including: (A) 20 are filled with SCA and BI's and labeled as indicated for the two BI types in the diagram below as illustrated in FIG. 5 with reference numbers 161, 162, 163, 164, 165, 166, 167, 168, 169, and 1610 indicating an example configuration for the 1-6100TT BI vials and 171, 172, 173, 174, 175, 176, 177, 178, 179, and 1710 indicating an example configuration for 3-6100TT BI vials; (B) 3 vials are filled with a medical adhesive, a 1-6100TT BI in medical adhesive, and a 3-6100TT BI in medical adhesive as controls—these vials do not go in the oven but are sent for testing with the above 20 BI vials; (C) 5 vials are filled with TEC with holes drilled in the caps for thermocouple placement and loaded in a configuration as illustrated in FIG. 5 with reference number 181, 182, 183, 184, and 185 indicating an example configuration; (D) dunnage vials are filled with water.

Twenty BI samples are placed in the sterilization tray 160 as shown in FIG. 5. Additionally, one control BI from the same lot as the previous 20 BIs is used as a control. Five thermocouples are used to monitor temperature at the four corners and the center of the sterilization tray 140. Water can be a viable substitute for the adhesive in the dunnage vials because water can have a higher heat capacity than some medical adhesives. TEC is used in the vials containing thermocouples because it has a 300° C. (testing runs at 125° C. max) boiling point to reduce blowing by thermocouple-to-vial seals at sterilization temperature.

In some embodiments, minimum conditions, half cycle testing for 1 hour 191 includes the following. The BI's are not refrigerator either before or after testing. Upon opening a BI, it is placed directly into the test vial. The BI is verified to be completely submerged in the medical adhesive before tightly screwing on vial cap. The oven is turned on to 110° C. and the alarm is set to 120° C. The vials are loaded on the tray as discussed above. Dunnage vials are verified to be 90%+ filled with tap water and the cap screwed on. Vials containing BIs are filled with medical adhesive and the cap screwed on. Vials containing thermocouples are filled with TEC and drilled through caps screwed on. In some embodiments, the vial initial temperature can start at between 17-35° C. When the oven temperature has reached the sterilization temperature, the baking sheet and tray are placed onto the third rack from the bottom of the oven and slid back until the baking sheet is in the middle of the oven. In some embodiments, the tray is placed into the oven during warm up to the sterilization temperature. Each thermocouple is connected to a thermometer. The timer is started once all thermocouples reach at least 105° C. Observations can be recorded every 15 minutes for 1 hour. The vials can remain at 110±5° C. once the temperature has been reached. Once the cycle is complete, the vials are allowed to return to room temperature. Once at room temperature, the BI-containing vials are sent to a lab for analysis.

In some embodiments, nominal conditions, half cycle testing for 1 hour 192 includes the following. The oven is turned on to 115° C. and the alarm is set to 125° C. The same procedures as discussed above for minimum conditions testing can be followed. The timer is started once all thermocouples reach at least 110° C. Observations can be recorded every 15 minutes for 1 hour. The vials can remain at 115±5° C. once the temperature has been reached.

In some embodiments, maximum conditions, half cycle testing for 1 hour 194 includes the following. The oven is turned on to 120° C. and the alarm is set to 130° C. The same procedures as discussed above for minimum conditions testing can be followed. The timer is started once all thermocouples reach at least 115° C. Observations can be recorded every 15 minutes for 1 hour. The vials can remain at 120±5° C. once the temperature has been reached.

In some embodiments, nominal conditions, full cycle testing for 2 hours 195 includes the following. The oven is turned on to 115° C. and the alarm is set to 125° C. The same procedures as discussed above for minimum conditions testing can be followed. The timer is started once all thermocouples reach at least 110° C. Observations can be recorded every 15 minutes for 2 hour. The vials can remain at 115±5° C. once the temperature has been reached.

Figure 7:
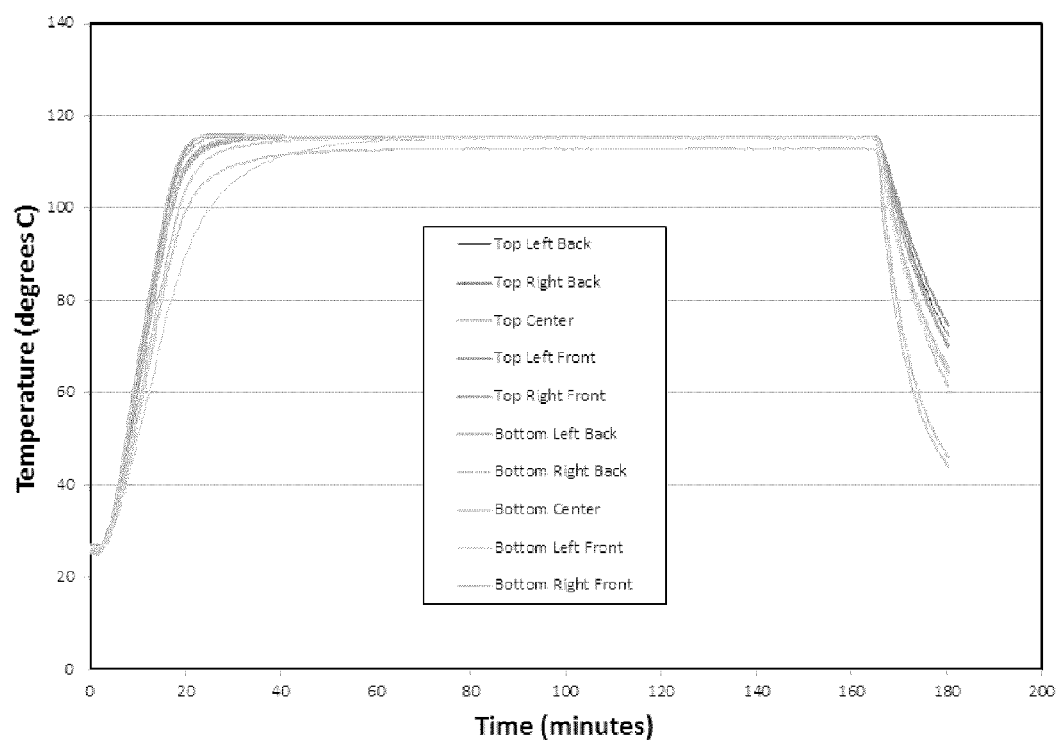
FIG. 7 illustrates a graph showing representative temperature profiles for an embodiment of a load configuration during a sterilization process.

FIG. 7 illustrates a graph showing representative temperature profiles for an embodiment of a load configuration in an oven during a sterilization process as discussed herein. In some embodiments, there are ten thermocouples for a given load configuration as in the above embodiments of FIGS. 4 and 5. For example, five vials are filled with TEC (triethyl citrate) with holes drilled in the caps for thermocouple placement and loaded in a configuration as illustrated in FIG. 4 with reference number 151, 152, 153, 154, and 155 indicating an example configuration. As another example, five vials are filled with TEC with holes drilled in the caps for thermocouple placement and loaded in a configuration as illustrated in FIG. 5 with reference number 181, 182, 183, 184, and 185 indicating an example configuration. In some embodiments, more or less than five thermocouples per tray may be used. Two trays can be loaded into the oven. In some embodiments, one or more than two trays may be loaded into the oven.

The temperature profile illustrated in FIG. 7 of the ten thermocouples shows that the vials are heated substantially uniformly throughout the sterilization process with an initial ramp-up period and post cool-down period as discussed herein. Substantially uniform temperature distribution helps ensure efficacy and validation of the sterilization process as discussed herein. In some embodiments, the thermocouples for a given load configuration stay within about a 10° C. range of each other. In some embodiments, the thermocouples for a given load configuration may stay within about a 5 to about 20° C., including about a 7 to about 15° C., range of each other, including ranges bordering and the foregoing values.

The foregoing procedures can produce one sterile lot of medical adhesive ready for first demand. After the vials that contained the BIs and thermocouples are discarded, the lot size 173 vials can be documented and stored in a cool, dry place. Some vials can undergo additional testing to ensure that the adhesive formulation still performs to the same standards as it did before the process.

In some embodiments, a full cycle time of about 4 hours can lead to the entire process to being done in one day. This can includes 2 hours for filling up the vials, 4 hours in the oven and 1 hour to cool down. Thus, in one work day the adhesive can easily go from a single container, to individual vials all sterilized by a validated process.

In some embodiments, the full cycle time can be about 2 hours which can lead to the entire process to being done in one day. This can includes 2 hours for filling up the vials, 2 hours in the oven and 1 hour to cool down. Thus, in one work day the adhesive can easily go from a single container, to individual vials all sterilized by a validated process. In some embodiments, the full cycle time can be less than 2 hours, between about 2 to about 4 hours, or more than 4 hours.

Running the process again incurs primarily the additional costs of powering the oven and to pay an employee a day's worth of wages. This can be due to the fact that all fixtures and trays being used in the process can be reused for every future run. Moreover, the cost of running the oven may be negligible.

With the process is in place, it can be used when needed. As per the standard, the oven can be dedicated to this process and as long as it is not moved to a different location, it can sterilize a new lot. If there are any changes in the formulation of the adhesive or if a new packaging method are established instead of the vials, further sterilization and/or validation processes may be developed. In either of these cases, a new validation may be executed in order to comply with ANSI standards. However, much of the work needed to be done for the validation will be completed already. The parameters and configuration can remain the same. But the PQ will need to be performed with whatever new changes to the formulation or vial that have been implemented.

In some embodiments, the process can be characterized as follows: (A) The whole cycle of filling the vials and sterilizing them can be completed in one 8-hour work day; (B) The lot size is large enough to meet needs without having to execute multiple runs; (C) The whole validation can be completed for a fraction of the cost compared to quotes received from vendors; (D) The established quality systems in place can be maintained; (E) The process can be validated per ANSI standards; and (F) One sterilized lot of medical adhesive can be ready for first demand clinical trials Sterilization of adhesives as disclosed herein and/or its packaging can be accomplished by various methods. These methods include chemical, physical, and/or irradiation methods. Examples of chemical methods include exposure to ethylene oxide or hydrogen peroxide vapor. Examples of physical methods include sterilization by heat. In some embodiments, an adhesive can be heat-sterilized at a temperature of less than about 170° C., 160° C., 150° C., 140° C., 130° C., 120° C., 110° C., or less. In one embodiment, an adhesive can be heat-sterilized at a temperature of between about 100° C. and 120° C. for less than about 240 minutes, 180 minutes, 150 minutes, 135 minutes, 120 minutes, 110 minutes, 100 minutes, 90 minutes, or less. Examples of irradiation methods include gamma irradiation, electron beam irradiation, and microwave irradiation.

The foregoing detailed description has set forth various embodiments of the systems and/or methods via the use of figures and/or examples. Insofar as such figures and/or examples contain one or more functions and/or operations, it will be understood by those within the art that each function and/or operation within figures or examples can be implemented individually and/or collectively. The herein-described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced embodiment recitation is intended, such an intent will be explicitly recited in the embodiment, and in the absence of such recitation no such intent is present. For example, as an aid to understanding, the disclosure may contain usage of the introductory phrases "at least one" and "one or more" to introduce embodiment recitations. However, the use of such phrases should not be construed to imply that the introduction of an embodiment recitation by the indefinite articles "a" or "an" limits any particular embodiment containing such introduced embodiment recitation to embodiments containing only one such recitation, even when the same embodiment includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce embodiment recitations. In addition, even if a specific number of an introduced embodiment recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, embodiments, or drawings, should be understood to contemplate the possibilities of including one of the terms, either of the terms, or both terms. For example, the phrase "A or B" will be understood to include the possibilities of "A" or "B" or "A and B."

Although the present invention has been described herein in terms of certain embodiments, and certain exemplary methods, it is to be understood that the scope of the invention is not to be limited thereby. Instead, the Applicant intends that variations on the methods and materials disclosed herein which are apparent to those of skill in the art will fall within the scope of the Applicant's invention.

What is claimed is:

1. A method for sterilizing a medical adhesive, the method comprising:
    enclosing the medical adhesive in a first housing;
    positioning the first housing with the medical adhesive in a tray, the tray configured to secure the first housing in a first predetermined position on the tray; and
    operating an oven at a predetermined temperature profile over a time duration to heat the medical adhesive to about the predetermined temperature profile over the time duration sufficient to sterilize the medical adhesive, wherein the predetermined temperature profile includes a temperature range of about 110° C. to about 120° C. and the time duration includes about 2 hours plus a ramp-up time of about 40 minutes, wherein following the sterilization process a post-sterilization viscosity of the medical adhesive is within about 10% or less of a pre-sterilization viscosity of the medical adhesive.

2. The method of claim 1, further comprising:
    enclosing a biological indicator in a second housing, the second housing configured to seal the biological indicator, the biological indicator configured to indicate whether sterilization has been achieved; and
    positioning the second housing with the biological indicator in the tray, the tray configured to secure the second housing in a second predetermined position on the tray.

3. The method of claim 2, wherein the biological indicator is enclosed in the second housing with the medical adhesive, and wherein the medical adhesive substantially surrounds the biological indicator.

4. The method of claim 1, further comprising:
    enclosing the medical adhesive in a first plurality of housings; and
    positioning the first plurality of housings with the medical adhesive in the tray, the tray configured to secure the first plurality of housing in a first plurality of predetermined positions on the tray.

5. The method of claim 4, wherein the first plurality of housing are heated to substantially a same temperature over the time duration.

6. The method of claim 5, wherein the first plurality of predetermined positions start at a center of the tray and radiate toward a perimeter of the tray as the first plurality of housing are positioned in the tray to help provide the same temperature over the time duration.

7. The method of claim 4, further comprising:
enclosing a substance not for patient application in a second plurality of housings; and
positioning the second plurality of housings with the substance in the tray, the tray configured to secure the second plurality of housing in a second plurality of predetermined positions on the tray,
wherein the second plurality of predetermined positions are substantially at a perimeter of the tray.

8. The method of claim 1, wherein the medical adhesive comprises a cyanoacrylate.

9. A method for sterilizing a medical adhesive, the method comprising:
enclosing the medical adhesive in a first housing, the first housing configured to seal the medical adhesive;
positioning the first housing with the medical adhesive in a tray, the tray configured to secure the first housing in a first predetermined position on the tray;
positioning the tray with the first housing on an oven rack, the oven rack inside an oven; and
operating the oven at a predetermined temperature profile over a time duration to heat the medical adhesive to about the predetermined temperature profile over the time duration sufficient to sterilize the medical adhesive, wherein the predetermined temperature profile includes a temperature range of about 110° C. to about 120° C. and the time duration includes about 2 hours, wherein following the sterilization process a post-sterilization viscosity of the medical adhesive is within about 10% or less of a pre-sterilization viscosity of the medical adhesive.

10. A method for sterilizing a medical adhesive, the method comprising:
enclosing the medical adhesive in a first housing, the first housing configured to seal the medical adhesive;
positioning the first housing with the medical adhesive within an oven; and
operating the oven to sterilize the medical adhesive, wherein following sterilization of the medical adhesive, a post-sterilization viscosity of the medical adhesive is within about 10% or less of a pre-sterilization viscosity of the medical adhesive.

11. The method of claim 10, further comprising:
enclosing a biological indicator in a second housing, the second housing configured to seal the biological indicator, the biological indicator configured to indicate whether sterilization of the medical adhesive has been achieved; and
positioning the second housing with the biological indicator within the oven.

12. The method of claim 11, wherein the biological indicator is enclosed in the second housing with the medical adhesive, and wherein the medical adhesive substantially surrounds the biological indicator.

13. The method of claim 10, wherein the medical adhesive comprises a cyanoacrylate.

14. The method of claim 10, wherein the oven is operated to have a ramp-up time of about 40 minutes to a predetermined temperature profile for sterilizing the medical adhesive.

15. The method of claim 10, further comprising:
operating the oven at a predetermined temperature profile that includes a temperature range of about 110° C. to about 140° C.

16. The method of claim 10, further comprising:
operating the oven at a predetermined temperature profile for a time duration of about 1 to 8 hours.

17. The method of claim 16, wherein the time duration includes a ramp-up time of up to 60 minutes.

18. The method of claim 16, wherein the predetermined temperature profile includes a temperature range of about 110° C. to about 120° C., and the time duration is about 2 to 7 hours.

19. The method of claim 18, wherein the oven is operated to have a ramp-up time of up to about 60 minutes to the predetermined temperature profile for sterilizing the medical adhesive.

20. The method of claim 10, wherein the medical adhesive is a cyanoacrylate.

* * * * *